United States Patent [19]

Umezawa et al.

[11] Patent Number: 4,537,880
[45] Date of Patent: Aug. 27, 1985

[54] AMINOPROPYLAMINOBLEOMYCIN DERIVATIVES AND PROCESS FOR PREPARATION THEREOF

[75] Inventors: Hamao Umezawa, Tokyo; Akio Fujii, Kanagawa; Yasuhiko Muraoka, Saitama; Tokuji Nakatani, Saitama; Takeyo Fukuoka, Saitama; Katsutoshi Takahashi, Tokyo, all of Japan

[73] Assignee: Zaidan Hojin Biseibutsu Kagaku Kenkyu Kai, Tokyo, Japan

[21] Appl. No.: 635,096

[22] Filed: Jul. 27, 1984

Related U.S. Application Data

[63] Continuation-in-part of Ser. No. 453,254, Dec. 27, 1982, abandoned.

[30] Foreign Application Priority Data

Dec. 29, 1981 [JP] Japan ................. 56-210449

[51] Int. Cl.³ ............ A61K 37/00; C07C 103/52
[52] U.S. Cl. ................. 514/19; 260/112.5 R
[58] Field of Search ............ 424/177; 260/112.5 R

[56] References Cited

U.S. PATENT DOCUMENTS

Re. 30,451 12/1980 Umezawa et al. .
3,922,262 11/1975 Umezawa et al. .
3,929,993 12/1975 Tomohisa et al. .

OTHER PUBLICATIONS

J. of Antibiotics, Umezawa, Maeda, et al., 19A, pp. 200-209 (1966).
J. of Antibiotics, Umezawa, Suhara, et al., 19A, pp. 210-215 (1966).

Primary Examiner—Delbert R. Phillips
Attorney, Agent, or Firm—Robert E. Carnahan

[57] ABSTRACT

An aminopropylaminobleomycin represented by the following formula or a salt thereof, which is minimized in side effects such as pulmonary toxicity:

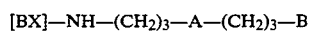

wherein
[BX] represents the acyl group of bleomycinic acid whose formula differs from that of bleomycin acid by the removal of the hydroxyl group from the carboxyl group of said acid;
A represents a group of the general formula

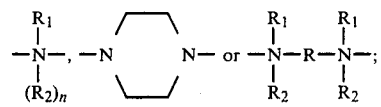

wherein
$R_1$ is a lower alkyl or benzyl,
$R_2$ is a lower alkyl or benzyl,
R is a lower alkylene, and
n is 0 or 1; and
B represents a group of the formula

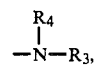

wherein
(i) $R_3$ is hydrogen and $R_4$ is
  (a) benzyl substituted by one or more halogen atoms, provided that the benzyl is substituted by two halogen atoms when $R_1$ is lower alkyl,
  (b) benzyl substituted by cyano, two or more alkoxy groups or two or more benzyloxy groups,
  (c) lower alkyl substituted by cycloalkyl or anthranyl,
  (d) phenylethyl substituted by one or more halogen atoms, or
  (e) diphenylethyl; or
(ii) both $R_3$ and $R_4$ are benzyl which may be substituted by one or more
  (a) benzyloxy groups,
  (b) ring substituted benzyloxy groups in which the ring substituents may be one or more halogen atoms, lower alkoxy groups or benzyloxy groups, or
  (c) cycloalkylmethoxy groups;
and a process for the preparation thereof.

10 Claims, No Drawings

AMINOPROPYLAMINOBLEOMYCIN DERIVATIVES AND PROCESS FOR PREPARATION THEREOF

CROSS-REFERENCE TO RELATED APPLICATION

This is a continuation-in-part of our copending application Ser. No. 453,254 filed Dec. 27, 1982, and now abandoned.

BACKGROUND OF THE INVENTION

This invention relates to novel aminopropylaminobleomycin derivatives.

The term bleomycin refers to a family of structurally related antitumor antibiotic substances discovered in 1966 by Umezawa, one of the present inventors, and collaborators [J. of Antibiotics, 19A, p. 200 (1966)]. Bleomycin is produced by *Streptomyces verticillus,* an Actinomycete, and is a mixture of basic water-soluble glycopeptides each of which is capable of readily chelating one atom of divalent copper. In ordinary culture, 16 members of the bleomycin family are produced and are each isolated [e.g. Umezawa et al., Journal of Antibiotics, 19A, p. 210 (1966)]. Various bleomycins are also disclosed in U.S. Pat. No. 3,922,262 and U.S. Pat. No. Re. 30,451. Because of their distinguished antitumor activity in spite of some undesirable side effects such as pulmonary toxicity, bleomycins have already been widely used in clinical fields of cancer therapy; particularly, they are successfully used in the treatment of squamous cell carcinoma as principal target, skin cancer, head and neck cancer, lung cancer, and malignant lymphoma. It is still desired, however, that bleomycins be further improved in antitumor activity and reduced in side effects, especially in pulmonary toxicity.

SUMMARY OF THE INVENTION

The present inventors paid attention to the fact that aminopropyl-N-methylaminopropylaminobleomycin (briefly APMP, described in U.S. Pat. No. Re. 30,451, Table 1, Number 22) strongly inhibits the growth of Hela Cell and conducted an extensive study to reduce the pulmonary toxicity of APMP. This invention is based on the discovery that it is possible to reduce remarkably the pulmonary toxicity by chemical modification of the terminal amino group of APMP with various substituted alkyl groups.

DETAILED DESCRIPTION OF THE INVENTION

The novel aminopropylaminobleomycin derivatives of this invention include both the copper-containing form and copper-free form and are represented by the general formula $$[BX]-NH-(CH_2)_3-A-(CH_2)_3-B \qquad (I)$$

wherein
[BX] is the acyl group having the formula formed by removal of the hydroxyl group from the carbonyl group of bleomycinic acid and is represented by the formula

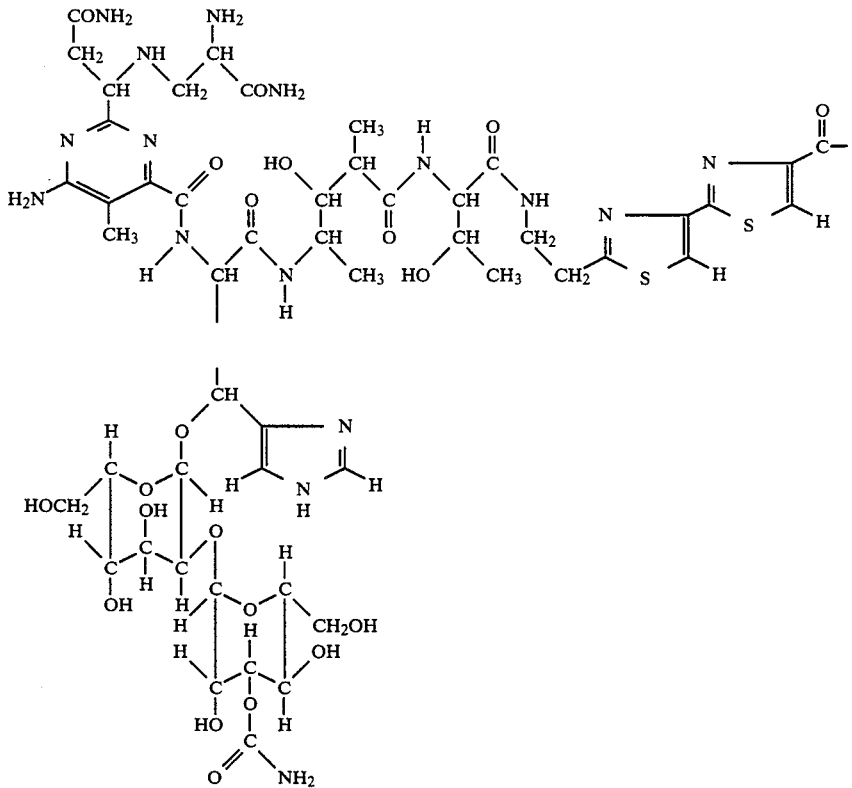

(copper is omitted in the case of copper-containing form). In Formula I A represents a group of the formula

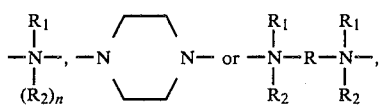

wherein
R₁ is a lower alkyl or benzyl,
R₂ is a lower alkyl or benzyl,
R is a lower alkylene,
n is 0 or 1; and
B represents a group of the formula

wherein
(i) R₃ is hydrogen and R₄ is
  (a) benzyl substituted by one or more halogen atoms, provided that the benzyl is substituted by two halogen atoms when R₁ is lower alkyl,
  (b) benzyl substituted by cyano, two or more alkoxy groups or two or more benzyloxy groups,
  (c) lower alkyl substituted by cycloalkyl or anthranyl,
  (d) phenylethyl substituted by one or more halogen atoms, or
  (e) diphenylethyl; or
(ii) both R₃ and R₄ are benzyl which may be substituted by one or more
  (a) benzyloxy groups,
  (b) ring substituted benzyloxy groups in which the ring substituents may be one or more halogen atoms, lower alkoxy groups or benzyloxy groups, or
  (c) cycloalkylmethoxy groups.

As examples for the lower alkyls, mention may be made of methyl, ethyl, n-propyl, isopropyl, n-butyl, and isobutyl; for the halogens, fluorine, chlorine, and bromine; for the lower alkylenes, ethylene, trimethylene, tetramethylene, pentamethylene, and hexamethylene; for the cycloalkyls, cyclopentyl, cyclohexyl, cycloheptyl, cyclooctyl, cyclodecanyl, cycloundecanyl, cyclododecanyl, and cyclotridecanyl; for the lower alkoxys, methoxy, ethoxy, propoxy, and butoxy; and for halomethyls, trifluoromethyl and trichloromethyl.

Examples of

in the above A are

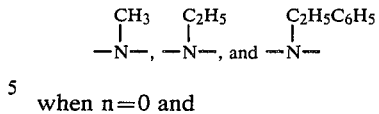

when n=0 and

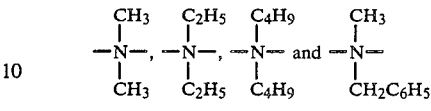

when n=1. Examples of

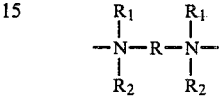

include

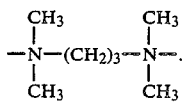

As examples of those compounds represented by the general formula (I) which are desirable from the standpoint of pharmacological activity, mention may be made of those compounds in which

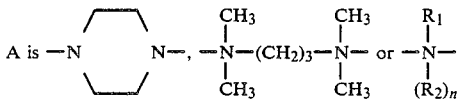

wherein
R₁ is a lower alkyl,
R₂ is a lower alkyl or benzyl,
n is 0 or 1; and
(i) R₃ is hydrogen and R₄ is
  (a) benzyl substituted by one or more halogen atoms, provided that the benzyl is substituted by two halogens when R₁ is lower alkyl,
  (b) benzyl substituted by cyano, two or more C₁–C₄ alkoxy groups or two or more benzyloxy groups,
  (c) methyl substituted by a C₈–C₁₃ cycloalkyl group, or
  (d) diphenylmethyl; or
(ii) both R₃ and R₄ are benzyl optionally substituted by one or more
  (a) benzyloxy groups which may contain one or more ring substituents selected from halogen atoms, C₁–C₄ alkoxy or benzyloxy, or
  (b) C₈–C₁₃ cycloalkylmethoxy groups.

Examples of representative compounds of this invention are as shown in Table 1.

TABLE 1

| Compound No. | Name of Compound | Abbreviation |
|---|---|---|
| 1 | 3-{N—Methyl-N—[3'-(2"-p-chlorophenylethylamino)propyl]amino}propylaminoBLM | MCLPE |
| 7 | 3-{N—Methyl-N—[3'-(m,p-dichlorobenzylamino)propyl]amino}propylaminoBLM | MDCLBZ(m,p) |
| 8 | 3-{N—Methyl-N—[3'-(o,p-dichlorobenzylamino)propyl]amino}propylaminoBLM | MDCLBZ(o,p) |
| 13 | 3-{N—Methyl-N—[3'-(o,p-dimethoxybenzylamino)propyl]amino}propylaminoBLM | MDMOBZ(o,p) |
| 14 | 3-{N—Methyl-N—[3'-(1"-p-chlorophenylethylamino)propyl]amino}propylaminoBLM | MCLAPE(p) |
| 15 | 3-{N—Methyl-N—[3'-(m,p-dibenzyloxybenzylamino)propyl]amino}propylaminoBLM | MDBZOBZ(m,p) |
| 17 | 3-{N—Methyl-N—[3'-(2",2"-diphenylethylamino)propyl]amino}propylaminoBLM | MDPE |

TABLE 1-continued

| Compound No. | Name of Compound | Abbreviation |
|---|---|---|
| 18 | 3-{N—Methyl-N—[3'-(p-cyanobenzylamino)propyl]amino}propylaminoBLM | MCNBZ |
| 21 | 3-{N—Methyl-N—[3'-(9-anthramethylamino)propyl]amino}propylaminoBLM | MANTRA |
| 22 | 3-{N—Methyl-N—[3'-(cyclooctylmethylamino)propyl]amino}propylaminoBLM | MCO |
| 27 | 3-{N—Methyl-N—[3'-(dibenzylamino)propyl]amino}propylaminoBLM | MDBZ |
| 28 | 3-{N—Methyl-N—[3'-(cyclopentylmethylamino)propyl]amino}propylaminoBLM | MCP |
| 29 | 3-{N—Methyl-N—[3'-(cyclohexylmethylamino)propyl]amino}propylaminoBLM | MCHM |
| 30 | 3-{N—Methyl-N—[3'-(cyclohexylethylamino)propyl]amino}propylaminoBLM | MCHE |
| 31 | 3-{N—Methyl-N—[3'-(cycloheptylmethylamino)propyl]amino}propylaminoBLM | MCHEP |
| 32 | 3-{N—Methyl-N—[3'-(cycloundecanylmethylamino)propyl]amino}propylaminoBLM | MCU |
| 34 | 3-{N—Methyl-N—[3'-(bis(m,p-dibenzyloxybenzyl)amino)propyl]amino}propylaminoBLM | MDDBZOBZ |
| 35 | 3-{N,N—Dimethyl-N—[3'-(dibenzylamino)propyl]amino}propylaminoBLM | MMDBZ |
| 36 | 3-{N,N—Dimethyl-N—[3'-(cyclooctylmethylamino)propyl]amino}propylaminoBLM | MMCO |
| 37 | 3-{N,N—Dimethyl-N—[3'-(dibenzylamino)propyl]amino}propylaminoBLM | EEDBZ |
| 38 | 3-{N,N—Dibutyl-N—[3'-(dibenzylamino)propyl]amino}propylaminoBLM | BBDBZ |
| 39 | 3-{N—Methyl-N—benzyl-N—[3'-(dibenzylamino)propyl]amino}propylaminoBLM | MTBZ |
| 40 | 3-{N—benzyl-N—[3'-(dibenzylamino)propyl]amino}propylaminoBLM | ATBZ |
| 41 | 3-{N,N—Dimethyl-N—[3'-(N,N—dimethyl-N—(3''-dibenzylaminopropyl)amino)propyl]amino}propylaminoBLM | PPDBZ |
| 42 | 3-{N,N—Dimethyl-N—[3'-(N,N—dimethyl-N—(3''-cyclooctylmethylaminopropyl)amino)propyl]amino}propylaminoBLM | PPCO |
| 43 | 3-[4-(3-dibenzylaminopropyl)piperazin-1-yl]propylamino)BLM | PYDBZ |
| 44 | 3-[4-(3-p-Chlorobenzylaminopropyl)piperazin-1-yl]propylaminoBLM | PYCLBZ |
| 45 | 3-[4-(3-Cyclooctylmethylaminopropyl)piperazin-1-yl]propylaminoBLM | PYCO |
| 46 | 3-{N,N—Diethyl-N—[3'-(2''-p-chlorophenylethylamino)propyl]amino}propylaminoBLM | EECLPE |
| 47 | 3-{N—Methyl-N—[3'-(cyclotridecanylmethylamino)propyl]amino}propylaminoBLM | MCT |
| 48 | 3-{N—Methyl-N—[3'-(bis(3'',4''di(p-chlorobenzyloxy)benzyl)amino)propyl]amino}propylaminoBLM | MDDCL |
| 49 | 3-{N—Methyl-N—[3'-(bis(3'',4''-di(m,p-dichlorobenzyloxy)benzyl)amino)propyl]amino}propylaminoBLM | MDDDCL |
| 50 | 3-{N—Methyl-N—[3'-(bis(3'',4''-di(p-methoxybenzyloxy)benzyl)aminopropyl]amino}propylaminoBLM | MDDMO |
| 51 | 3-{N—Methyl-N—[3'-(bis(4''-(p-benzyloxy)benzyl)amino)propyl]amino}propylaminoBLM | MDBZOBZOBZ |
| 52 | 3-{N—Methyl-N—[3'-(bis(p-cyclooctylmethyloxybenzyl)amino)propyl]amino}propylaminoBLM | MDCDBZ |
| 53 | 3-{N—Methyl-N—[3'-(bis(3'',4'',5''-tribenzyloxybenzyl)amino)propyl]amino}propylaminoBLM | MDTBZOBZ |

NOTE:
"BLM" stands for "bleomycin".

The compounds of this invention represented by the general formula (I) are prepared by allowing an aminopropylaminobleomycin of the formula

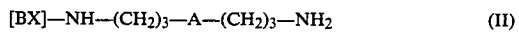

$$[BX]—NH—(CH_2)_3—A—(CH_2)_3—NH_2 \quad (II)$$

wherein

[BX] and A are as defined above, to condense reductively with a carbonyl compound of the formula

$$R_5—CO—R_6 \quad (III)$$

wherein $R_5$ and $R_6$ are independently (1) a hydrogen atom, (2) a cycloalkyl, (3) an alkyl which may be substituted by one or more cycloalkyl or phenyl groups (the phenyl group may be substituted by a halogen atom, (4) phenyl which may be substituted by one or more halogen atoms or lower alkyl, cycloalkylmethyloxy, lower alkoxy, benzyloxy, cyano, halomethyl, halobenzyloxy, (lower)alkoxybenzyloxy, or benzyloxybenzyloxy groups, (5) anthranyl; provided that at least either one of $R_5$ and $R_6$ is a group other than hydrogen atom.

The reducing agents used in the condensation include borohydride compounds such as sodium cyanoborohydride. The condensation can also be effected by the catalytic hydrogenation using a catalyst such as palladium-carbon. The amount used of the carbonyl compound varies depending upon the type of intended product and cannot be unconditionally generalized, but broadly it is in the range of from 0.5 to 25, usually from 0.7 to 20, moles for 1 mole of the compound of formula (II). A derivative in which $R_4$ is hydrogen atom is chiefly obtained by using 1 to 1.5 moles of the carbonyl compound, while a derivative in which $R_3$ and $R_4$ are the same group is obtained when 10 moles of it is used. When a derivative in which $R_1$, $R_3$, and $R_4$ are the same group (e.g. Compound No. 40) is intended, 15 moles of the carbonyl compound is used. If the compound of formula (III) is difficulty soluble in methanol, as is the case with m,p-dibenzyloxybenzaldehyde for example, its amount can be reduced by prolonging the reaction time. The condensation is carried out in a solvent such as methanol, water, dimethylformamide, acetonitrile, or a mixture thereof. Although depending upon the type of intended product, the reaction temperature is generally $-5°$ to $70°$ C., preferably $0°$ to $50°$ C. It is $0°$ to $25°$ C. when $R_4$ of the intended derivative is hydrogen, while a higher temperature such as $35°$ to $50°$ C. is preferred when use is made of a ketone, or an aldehyde in which $R_3$ and $R_4$ are the same and of a high steric hindrance, or an aldehyde of low solubility. The reaction time is 3 to 70 hours. A longer reaction time is advantageous for the condensation when an aldehyde of higher steric hindrance or of low solubility is used.

The isolation of the present derivative obtained as described above is carried out in the following manner.

When a borohydride compound is used as the reducing agent, the reaction mixture is adjusted to pH 1 with hydrochloric acid, stirred for 5 to 10 minutes at room temperature to decompose the excess reducing agent, then neutralized, removed of methanol by distillation under reduced pressure, and extracted with ether or butanol to remove the excess aldehyde or ketone. The aqueous layer is desalted by passing through a column packed with an adsorptive resin such as, for example, Amberlite®XAD-2 (Rohm and Haas Co.) in distilled water to effect adsorption of the intended product to the resin. After washing the column with distilled water to wash off the salt, the adsorbed material is eluted with an acidic aqueous methanol such as, for example, a 1/50N aqueous hydrochloric acid-methanol (1:4 v/v)

mixture to collect the eluate fractions containing a blue bleomycin derivative. The combined fraction is neutralized, if necessary, with Dowex ®44 (an OH-type anion exchange resin of Dow Chemical Co.), then concentrated under reduced pressure, and lyophilized to yield a crude blue powder of the intended derivative. In order to improve the purity, the crude powder is treated in the following manner.

A solution of the crude powder in distilled water is passed through a column packed with CM-Sephadex ®C-25 (Na+ type; Pharmacia Fine Chemicals Co.), which has been equilibrated with a 1/20M acetic acid-sodium acetate buffer solution of pH 4.5, to effect adsorption of the intended product onto the resin. The adsorbed phase is then eluted by the linear concentration gradient technique which is carried out by continuously adding sodium chloride to the above buffer solution to increase gradually the sodium chloride concentration to 1.0M. If the eluate fractions containing the intended product are found to be still contaminated with impurities, the above-noted chromatography is followed by another chromatography using an adsorptive resin such as, for example, Amberlite ®XAD-2, which is carried out by passing a solution of crude substance in distilled water through a column packed with the resin in a buffer solution such as, for example, a 4% aqueous ammonium acetate solution, to effect adsorption of the intended product to the resin, and eluting the adsorbed phase by the linear concentration gradient method which is carried out by continuously adding methanol to the buffer solution to increase gradually the methanol concentration. In this case, the elution feature is such that the unreacted starting materials are eluted at first, then followed by a derivative in which $R_4$ is hydrogen, and finally by a derivative in which $R_3$ and $R_4$ are the same group. The separation of the fractions is possible by using an ultraviolet monitor. If the intended fraction still contained the impurities, the above chromatography should be repeated to achieve complete removal.

The combined fraction containing the intended product is freed from the methanol by distillation under reduced pressure, desalted by using Aberlite ®XAD-2, and lyophilized to yield a blue amorphous powder of a copper-containing aminopropylaminobleomycin derivative. The copper-free form is obtained by removing the copper from the copper-containing form by a known method such as the method employing EDTA (Japanese Patent Publication No. 31,875/77; U.S. Pat. No. 3,929,993). An example of the copper-removing procedure is described below.

The copper-containing product is dissolved in distilled water and the resulting solution is passed through a column packed with Amberlite ®XAD-2 in distilled water to effect adsorption of the intended product. The column of resin is then washed with an aqueous solution containing sodium chloride and 5% of disodium salt of ethylenediaminetetraacetic acid (briefly EDTA.2Na) to carry away the copper ion by EDTA.2Na, leaving behind the copper-free aminopropylaminobleomycin adsorbed to the resin. The resin is washed with a sodium chloride solution to remove EDTA.2Na, then with distilled water, and finally eluted with an acidic aqueous methanol such as, for example, a 1/50N aqueous hydrochloric acid-methanol (1:4 v/v) mixture to collect the fractions which show an adsorption maximum at 290 mμ. The combined fraction is adjusted to pH 6.0 with Dowex ®44 (OH-type; Dow Chemical Co.), concentrated under reduced pressure, and lyophilized to yield a white amorphous powder of an aminopropylaminobleomycin in the form of copper-free hydrochloride. If an aqueous sulfuric acid is used in place of the aqueous hydrochloric acid, there is obtained a sulfate. Thus, it is possible to obtain a desired salt by selecting the acid used in the elution step.

Upon hydrolysis with 6N aqueous hydrochloric acid at 105° C. for 20 hours, the aminopropylaminobleomycin derivative prepared as described above gave those decomposition products which are common to bleomycins, including L-threonine, β-amino-β-(4-amino-6-carboxy-5-methylpyrimidin-2-yl)propionic acid, 4-amino-3-hydroxy-2-methyl-n-pentanoic acid, β-hydroxy-L-histidine, β-amino-L-alanine, and 2'-(2-aminoethyl)-2,4'-bithiazole-4-carboxylic acid, beside amine compounds. On the other hand, upon the methanolysis with Amberlite ®15 the aminopropylaminobleomycin derivative gave, as in the case of bleomycin, L-gulose and methylglucoside of 3-O-carbamoyl-D-mannose, as detected by gas chromatography. The above facts support that the chemical structure of the aminopropylaminobleomycin derivative prepared according to the process of this invention is as shown by the aforementioned general formula (I).

As the compounds of formula (II), which are a starting material for the synthesis of the present bleomycin derivatives, mention may be made of (1) 3-[N-(3-aminopropyl)amino]propylaminobleomycin (APP, described in U.S. Pat. No. Re. 30,451, Table 1, Number 48), (2) 3-[N-(3-aminopropyl)-N-methylamino]propylaminobleomycin (APMP), (3) 3-[N-(3-aminopropyl)-N,N-dimethylamino]propylaminobleomycin (MMHH), (4) 3-[N-(3-aminopropyl)-N,N-diethylamino]propylaminobleomycin (EEHH), (5) 3-[N-(3-aminopropyl)-N,N-dibutylamino]propylaminobleomycin (BBHH), (6) 3-{N-[3'-(N'-(3-aminopropyl)-N',N'-dimethylamino)-propyl]-N,N-dimethylamino}propylaminobleomycin (PP4M), (7) 3-[4-(3-aminopropyl)piperazin-1-yl]propylaminobleomycin (PY, described in U.S. Pat. No. Re. 30,451, Table 1, Number 28), and (8) 3-[N-(3-aminopropyl)-N-methyl-N-benzylamino]propylaminobleomycin (MBZHH) (the letters in parentheses are abbreviations). These compounds are synthesized by (1) condensing bleomycinic acid with a compound represented by the general formula (IV)

$$NH_2—(CH_2)_3—A—(CH_2)_3—NH_2 \qquad (IV)$$

wherein A is as defined previously, in a manner similar to that in a known method [for example, a method described in Japanese Patent Application "Kokai" (Laid-open) No. 63,089/79; or by (2) culturing in the presence of an amine of the formula (IV) a bleomycin-producing strain of Streptomyces verticillus such as, for example, Streptomyces verticillus NK-68-144 (ATCC 31307) as disclosed in U.S. Pat. No. Re. 30,451. Examples of the compounds represented by the formula (IV) include (1) bis(3-aminopropyl)amine, (2) bis(3-aminopropyl)methylamine, (3) bis(3-aminopropyl)dimethylammonium salt, (4) bis(3-aminopropyl)diethylammonium salt, (5) bis(3-aminopropyl)dibutylammonium salt, (6) 1,3-[bis(3-aminopropyl)dimethylamino]propane, (7) 1,4-[bis(3-aminopropyl)]piperazine, and (8) bis(3-aminopropyl)(methyl)benzylammonium salt.

Among the compounds of formula (IV), those represented by the following general formula (IVa) or (IVb)

are novel compounds first synthesized by the present inventors:

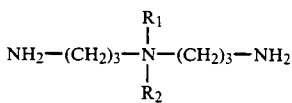

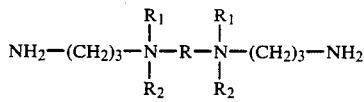

wherein $R_1$, $R_2$ and R are as defined above. These compounds are prepared, for example, by the following procedures.

A compound of the formula (IVa) in which $R_1$ and $R_2$ are the same group is prepared by reacting a 3-aminopropyl-N,N-dialkylamine represented by the general formula

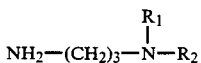

(wherein $R_1$ and $R_2$ are the same group and are as defined above) with 1.5 equivalents of benzoyl chloride, adding an alkali to the reaction mixture to make it alkaline, extracting the mixture with an organic solvent to obtain a 3-benzamidopropyl-N,N-dialkylamine represented by the general formula

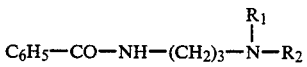

(wherein $R_1$ and $R_2$ are the same group and are as defined above), then reacting this amine with N-(3-bromopropyl)phthalimide to convert the amine into a quaternary ammonium salt of the general formula

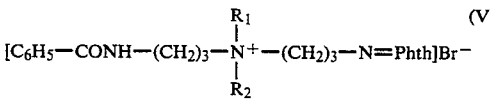

(wherein Phth stands for phthalyl group; $R_1$ and $R_2$ are the same group and are as defined above), hydrolyzing the quaternary salt by heating with 6N hydrochloric acid at 110° C. for 8 hours, removing the phthalic acid and benzoic acid formed as by-products, concentrating the hydrolyzate mixture to remove the hydrochloric acid as far as possible, dissolving the residue in distilled water, passing the solution through a column of an anion exchange (Cl-type), and concentrating the effluent to yield hydrochloride of the compound of formula (IVa) in which $R_1$ and $R_2$ are the same group. As examples of compounds prepared by the above procedure, mention may be made of bis(3-aminopropyl)dimethylammonium salt, bis(3-aminopropyl)diethylammonium salt, and bis(3-aminopropyl)dibutylammonium salt.

Another compound of the formula (IVa) in which $R_1$ and $R_2$ are different groups is prepared, for example, by reacting N-methylbenzylamine with 2 equivalents of 3-bromopropylphthalimide in the presence of a base and hydrolyzing the resulting quaternary ammonium salt as described above. An example of the compound prepared by this procedure is bis(3-aminopropyl)(methyl)benzylammonium salt.

A compound of the formula (IVb) is prepared, for example, by reacting 1,3-bis(dimethylamino)propane with 3-bromopropylphthalimide to form 1,3-[bis(3-phthalimidopropyl)dimethylamino]propane, hydrolyzing the resulting compound as described above, removing phthalic acid, a by-product, from the hydrolyzate mixture, subjecting the mixture to ion exchange, and concentrating. An example of the compound prepared by this procedure is 1,3-[bis(3-aminopropyl)dimethylamino]propane tetrahydrochloride.

The compounds of general formula (III), used as another starting material, include p-chlorophenylacetaldehyde, phenylacetaldehyde, benzaldehyde, p-chlorobenzaldehyde, m-chlorobenzaldehyde, o-chlorobenzaldehyde, m,p-dichlorobenzaldehyde, o,p-dichlorobenzaldehyde, p-fluorobenzaldehyde, p-bromobenzaldehyde, pentafluorobenzaldehyde, p-methoxybenzaldehyde, o,p-dimethyloxybenzaldehyde, p-chlorophenylmethyl ketone, m,p-dibenzyloxybenzaldehyde, 3-phenylpropanal, diphenylacetaldehyde, p-cyanobenzaldehyde, m-trifluoromethylbenzaldehyde, 1,3-diphenylacetone, acetophenone, cyclohexanone, 2-cyclohexylacetaldehyde, anthracene-9-aldehyde, cycloctanecarbaldehyde, cyclopentanecarbaldehyde, cyclohexanecarbaldehyde, cycloheptancarbaldehyde, cyclooctanecarbaldehyde, cycloundecanecarbaldehyde, m,p-dibenzyloxybenzaldehyde, cyclotridecanecarbaldehyde, 3,4-di(p-chlorobenzyloxy)benzaldehyde, 3,4-di(m,p-dichlorobenzyloxy)benzaldehyde, 3,4-di(p-methoxybenzyloxy)benzaldehyde, 4-(p-benzyloxybenzyloxy)benzaldehyde, p-cyclooctylmethyloxybenzaldehyde, and 3,4,5-tribenzyloxybenzaldehyde. Of these compounds novel compounds are 3,4-di(p-chlorobenzyloxy)benzaldehyde, 3,4-di(3',4'-dichlorobenzyloxy)benzaldehyde, 3,4-di(p-methoxybenzyloxy)benzaldehyde, 4-(4'-benzyloxybenzyloxy)benzaldehyde, and 4-cyclooctylmethyloxybenzaldehyde. These are prepared in the following manner.

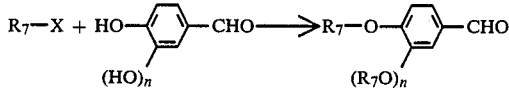

wherein
$R_7$ is p-methoxybenzyl, 3,4-dichlorobenzyl, p-chlorobenzyl, p-benzyloxybenzyl, or cyclooctylmethyl,
X is a halogen, and
n is 0 or 1.

A compound of the formula (VIII) and a compound of the formula (IX) are allowed to react in a solvent such as acetone at a temperature from room temperature to the boiling point of the solvent. After completion of the reaction, the reaction mixture is stripped of the solvent by distillation and admixed with water and an organic solvent to transfer the aldehyde to the organic phase. If necessary, the crude product obtained from the organic phase is purified by recrystallization or by column chromatography using silica gel or an adsorptive resin to obtain a pure product.

The cyclotridecanecarbaldehyde listed above is also a novel compound which is prepared in the following manner: Titanium tetrachloride is added to a mixture of zinc dust, anhydrous tetrahydrofuran and dibromomethane. To the resulting mixture is added cyclotridecanone to yield methylene cyclotridecane which is then epoxidized with m-chloroperbenzoic acid. After purification, the epoxidized product is reacted with boron trifluoride-ether complex in anhydrous dichloromethane to yield cyclotridecanecarbaldehyde.

The physicochemical properties of the representative aminopropylaminobleomycin derivatives of this invention are as shown in Table 2.

(2) Growth inhibitory activity against Hela $S_3$ cells

Hela $S_3$ cells were inoculated into a medium (MEM containing 10% of calf serum) placed in a plastic Petri dish. Two days after the inoculation, the Bleomycin derivative being tested was added to the medium and incubation was continued for further 3 days when the number of cells was counted. The percentage growth inhibition was calculated using the equation:

TABLE 2

| Compound No. | Abbreviation | Ultraviolet absorption maximum of copper-free compound, mμ (E 1%/1 cm) | *1 TLC of Cu—containing compound, Rq | *2 Electrophoresis of Cu—containing compound, Rm (Rm of alanine = 1.0) |
|---|---|---|---|---|
| 1 | MCLPE | 291 (87) | 0.75 | 1.01 |
| 7 | MDCLBZ(m,p) | 291 (89) | 0.72 | 1.02 |
| 8 | MDCLBZ(o,p) | 291 (89) | 0.75 | 0.99 |
| 13 | MDMOBZ(o,p) | 283 (100) | 0.83 | 0.97 |
| 14 | MCLAPE(p) | 291 (88) | 0.76 | 1.04 |
| 15 | MDBZOBZ(m,p) | 285 (65) | 0.55 | 0.90 |
| 17 | MDPE | 291 (89) | 0.72 | 1.07 |
| 18 | MCNBZ(p) | 291 (95) | 0.83 | 1.08 |
| 21 | MANTRA | 352 (24) 290 (73) 254 (571) | 0.66 | 0.85 |
| 22 | MCO | 291 (86) | 0.72 | 1.02 |
| 27 | MDBZ | 291 (88) | 0.65 | 1.00 |
| 28 | MCP | 291 (91) | 0.81 | 1.13 |
| 29 | MCHM | 291 (91) | 0.78 | 1.11 |
| 30 | MCHE | 291 (90) | 0.72 | 1.04 |
| 31 | MCHEP | 291 (90) | 0.74 | 1.01 |
| 32 | MCU | 291 (87) | 0.54 | 0.99 |
| 34 | MDDBZOBZ | 285 (86) | 0.12 | 0.75 |
| 35 | MMDBZ | 291 (87) | 0.67 | 0.99 |
| 36 | MMCO | 291 (90) | 0.71 | 0.98 |
| 37 | EEDBZ | 291 (90) | 0.60 | 1.03 |
| 38 | BBDBZ | 291 (87) | 0.45 | 0.99 |
| 39 | MTBZ | 291 (83) | 0.55 | 0.97 |
| 40 | ATBZ | 291 (87) | 0.50 | 0.96 |
| 41 | PPDBZ | 291 (84) | 0.69 | 1.11 |
| 42 | PPCO | 291 (87) | 0.52 | 1.12 |
| 43 | PYDBZ | 291 (93) | 0.67 | 0.95 |
| 44 | PYCLBZ | 291 (99) | 0.80 | 1.01 |
| 45 | PYCO | 291 (99) | 0.74 | 0.98 |
| 46 | EECLPE | 291 (82) | 0.72 | 1.11 |
| 47 | MCT | 292 (99) | 0.43 | 1.06 |
| 48 | MDDCL | 286 (101) | 0.04 | 0.17 |
| 49 | MDDDCL | 284 (82) | 0.01 | 0.02 |
| 50 | MDDMO | 280 (93) | 0.15 | 0.87 |
| 51 | MDBZOBZOBZ | 282 (84) | 0.08 | 0.21 |
| 52 | MDCOBZ | 287 (87) | 0.02 | 0.51 |
| 53 | MDTBZOBZ | 294 (61) | 0.01 | 0.19 |

NOTE:
*1 Silica gel 60F 254 silanised ® (Merck Co.); methanol - 6% ammonium acetate solution (60:40 v/v).
*2 Avicel SF ® (FMC Co.); formic acid-acetic acid-water (27; 75:900 v/v), 800 v, 15 minutes.

The biological properties of typical examples of the compounds of this invention are described below.

(1) Antimicrobial activity against *Mycobacterium smegmatis* ATCC 697 and *Bacillus subtilis*

The activity was assayed against the above test microorganisms by the method of agar plate-cylinder, assuming the potency of bleomycin $A_2$ (Cu-free form), used as standard, to be 1,000 mcg/mg.

Percentage growth inhibition (in %) = $100 \times (B-A)/(B-C)$ wherein A is the ultimate number of cells on the third day from the addition of a test sample, B is the ultimate number of cells in the control (without the addition of test sample), and C is the number of cells on the day of addition of the test sample. $ID_{50}$ (concentration of 50% inhibition) was estimated from the curve of sample concentration vs. percentage inhibition.

The test results obtained in (1) and (2) were as shown in Table 3.

TABLE 3

| Compound | | Antimicrobial potency of Cu—free compound, mcg potency per mg | | 50% growth inhibition concentration ($ID_{50}$) of Cu—free compound against cultured Hela cell, mcg/ml |
|---|---|---|---|---|
| | | Against *Mycobacterium smegmatis* ATCC 607 | Against *Bacillus subtilis* | |
| No. | Abbreviation | | | |
| 1 | MCLPE | 16800 | 13266 | 0.54 |

TABLE 3-continued

| Compound | | Antimicrobial potency of Cu—free compound, mcg potency per mg | | 50% growth inhibition concentration (ID$_{50}$) of Cu—free compound against cultured Hela cell, mcg/ml |
|---|---|---|---|---|
| No. | Abbreviation | Against *Mycobacterium smegmatis* ATCC 607 | Against *Bacillus subtilis* | |
| 7  | MDCLBZ(m,p)  | 10601 | 4263  | 0.82 |
| 8  | MDCLBZ(o,p)  | 13013 | 2940  | 1.05 |
| 13 | MDMOBZ(o,p)  | 5351  | 5312  | 1.30 |
| 14 | MCLAPE(p)    | 16959 | 5459  | 0.52 |
| 15 | MDBZOBZ(m,p) | 4516  | 1772  | 0.36 |
| 17 | MDPE         | 21084 | 3554  | 1.00 |
| 18 | MCNBZ        | 3163  | 4347  | 1.10 |
| 21 | MANTRA       | 13250 | 4504  | 0.80 |
| 22 | MCO          | 22860 | 12300 | 0.45 |
| 27 | MDBZ         | 14194 | 1138  | 0.89 |
| 28 | MCP          | 13595 | 16180 | 1.00 |
| 29 | MCHM         | 15414 | 12148 | 0.63 |
| 30 | MCHE         | 35030 | 14440 | 0.56 |
| 31 | MCHEP        | 25924 | 20143 | 0.48 |
| 32 | MCU          | 28308 | 8146  | 0.58 |
| 34 | MDDBZOBZ     | 164   | 49    | 0.38 |
| 35 | MMDBZ        | 13784 | 1742  | 0.87 |
| 36 | MMCO         | 21840 | 20000 | 0.29 |
| 37 | EEDBZ        | 10680 | 1047  | 0.70 |
| 38 | BBDBZ        | 17910 | 530   | 2.00 |
| 39 | MTBZ         | 7746  | 580   | 2.30 |
| 40 | ATBZ         | 4450  | 479   | 1.90 |
| 41 | PPDBZ        | 16000 | 7100  | 0.66 |
| 42 | PPCO         | 26000 | 14600 | 0.51 |
| 43 | PYDBZ        | 14420 | 1230  | 0.50 |
| 44 | PYCLBZ       | 11350 | 6080  | 0.31 |
| 45 | PYCO         | 43000 | 15100 | 0.81 |
| 46 | EECLPE       | 17480 | 13310 | 0.52 |
| 47 | MCT          | 3915  | 1760  | 0.18 |
| 48 | MDDCL        | 14    | 8     | 0.058 |
| 49 | MDDDCL       | 23    | 8     | 0.063 |
| 50 | MDDMO        | 145   | 35    | 0.70 |
| 51 | MDBZOBZOBZ   | 163   | 46    | 0.12 |
| 52 | MDCOBZ       | 268   | 49    | 0.13 |
| 53 | BMDTBZOBZ    | 11    | 26    | 0.062 |

It is seen from Table 3 that the compound of this invention has a strong growth inhibitory activity against cultured Hela cells as well as a strong antimicrobial activity.

(3) Pulmonary toxicity (pulmonary fibrosis) in mice

A. Intraperitoneal Injection

ICR strain mice (male; 15 weeks old; 9 mice per group) were used. Each mouse was administered with a daily dose of 5 mg/kg of the test sample by intraperitoneal injection, once a day, for 10 consecutive days. After completion of the predetermined administration, the mice were kept for 5 weeks under observation, then slaughtered, and autopsied to examine the incidence and grade of pulmonary fibrosis. The evaluation was made by comparing the number of administered mice suffering from pulmonary fibrosis and the grade of the disease. The results of examination were as shown in Table 4A.

The "ratio" was calculated by comparison with "bleomycin complex".

TABLE 4A

| Compound | Incidence | | | Grade | | |
|---|---|---|---|---|---|---|
| | Number of mice suffering from pulmonary fibrosis | % | Ratio | Total score of pulmonary fibrosis/total number of test animal | % | Ratio |
| 1  | 2/9  | 22  | 0.35  | 3/27  | 11 | 0.13 |
| 7  | 1/9  | 11  | 0.18  | 1/27  | 4  | 0.05 |
| 8  | 1/9  | 11  | 0.18  | 2/27  | 7  | 0.08 |
| 13 | 2/6  | 33  | 0.53  | 2/18  | 11 | 0.13 |
| 14 | 2/9  | 22  | 0.35  | 3/27  | 11 | 0.13 |
| 15 | 1/9  | 11  | 0.18  | 1/27  | 4  | 0.05 |
| 17 | 1/5  | 20  | 0.32  | 1/15  | 7  | 0.08 |
| 18 | 0/9  | 0   | 0.00  | 0/27  | 0  | 0.00 |
| 22 | 0/9  | 0   | 0.00  | 0/27  | 0  | 0.000 |
| 27 | 1/5  | 20  | 0.32  | 1/15  | 7  | 0.08 |
| 32 | 0/9  | 0   | 0.00  | 0/27  | 0  | 0.00 |
| 34 | 0/9  | 0   | 0.00  | 0/27  | 0  | 0.00 |
| 35 | 0/9  | 0   | 0.00  | 0/27  | 0  | 0.00 |
| 38 | 0/9  | 0   | 0.00  | 0/27  | 0  | 0.00 |
| 39 | 0/9  | 0   | 0.00  | 0/27  | 0  | 0.00 |
| 41 | 0/9  | 0   | 0.00  | 0/27  | 0  | 0.00 |
| 42 | 0/9  | 0   | 0.00  | 0/27  | 0  | 0.00 |
| 43 | 0/9  | 0   | 0.00  | 0/27  | 0  | 0.00 |
| 44 | 0/9  | 0   | 0.00  | 0/27  | 0  | 0.00 |
| 45 | 0/9  | 0   | 0.00  | 0/27  | 0  | 0.00 |
| 46 | 0/9  | 0   | 0.00  | 0/27  | 0  | 0.00 |
| 47 | 0/9  | 0   | 0.00  | 0/27  | 0  | 0.00 |
| 48 | 0/9  | 0   | 0.00  | 0/27  | 0  | 0.00 |
| 49 | 0/9  | 0   | 0.00  | 0/27  | 0  | 0.00 |
| 50 | 0/9  | 0   | 0.00  | 0/27  | 0  | 0.00 |
| 51 | 0/9  | 0   | 0.00  | 0/27  | 0  | 0.00 |
| 52 | 0/9  | 0   | 0.00  | 0/27  | 0  | 0.00 |
| 53 | 0/9  | 0   | 0.00  | 0/27  | 0  | 0.00 |
| APMP | 9/9 | 100 | 1.6  | 48/27 | 0  | 2.15 |

It is seen from Table 4A that some of the present compounds show entirely no occurrence of pulmonary fibrosis after intraperitoneal injection, and that even in cases where the fibrosis is observed the degree of pulmonary toxicity is greatly reduced, the incidence being less than about one-half and the grade less than about one-seventh of those exhibited by APMP-BLM. Since it has heretofore been very difficult to eliminate the side effects of bleomycins, particularly pulmonary fibrosis, it is a surprising fact that this invention provides a compound which exhibits no side effect leading to pulmonary fibrosis, though in an animal test.

B. Intratracheal Instillation

Male 15 weeks old ICR mice were used. Sixteen μg/50 μl/mouse of each test sample was intratracheally instilled. The mice were sacrificed 4 weeks after instillation to examine the incidence and grade of pulmonary fibrosis. The evaluation was made by comparing the number of administered mice suffering from pulmonary fibrosis and the grade of the disease.

The results of these tests are shown in Table 4B.

TABLE 4B

| Compound | Incidence Number of mice with pulmonary fibrosis/ number of mice (%) | Grade Total score of pulmonary fibrosis/total number of samples (%) |
|---|---|---|
| No. 7 | 3/10 (30) | 4/30 (13) |
| 8 | 2/8 (25) | 6/24 (25) |
| 13 | 2/9 (22) | 4/27 (15) |
| 14 | 4/7 (57) | 5/21 (24) |
| 15 | 1/8 (13) | 1/24 (4) |
| 17 | 2/9 (22) | 2/27 (7) |
| 27 | 2/9 (22) | 2/27 (7) |
| 35 | 2/8 (25) | 2/24 (8) |
| 39 | 2/9 (22) | 4/27 (15) |
| PEP | 6/8 (75) | 36/24 (150) |
| PEPP | 8/9 (89) | 15/27 (56) |
| MNBZ | 8/9 (89) | 28/27 (104) |

Reference compounds for Table 4B:
PEP: (3-[(S)—1'-phenylethylamino]propylamino-bleomycin (described in reference A)
PEPP: 3-[3-(N—1-phenylethyl)aminopropyl]aminopropylamino-bleomycin (described in reference AA: compound No. 15)
MNBZ: 3-(N—methyl-N—3-p-nitro-benzylamino-propyl)aminopropylamino-bleomycin (described in reference AB: compound No. 113)

The reason that the above compounds were selected is as follows:

PEP is used in clinical fields.

PEPP and MNBZ seem to be the nearest to our compounds in structure in the compounds described in cited references.

As is apparent from Table 4B that, compared with the case of PEP, PEPP and MNBZ, fibrosis due to our said compounds was reduced to about less than 1/6, ½ and ¼, respectively, in grade.

In Table 4B, the data in grade and the data (except compound Nos. 14 and 8) in incidence are beyond the range of expected variation of test results.

And, showing that our said compounds have remarkably low pulmonary toxicity as compared with a commercial PEP, the data of Table 4B indicates the usefulness of our compounds in clinical fields. In Tables 4A and 4B, the grade was numerically rated as follows:

0 point: No fibrosis.
1 point: Accumulation of exudate in pulmonary alveoli and fibrosis-like change in alveolar septum.
2 points: Fibrosis in several areas.
4 points: Scattered fibrosis.
6 points: Fibrosis in more than two-thirds of the total area.

In Vivo Antitumor Activity

The following data with respect to the testing of a group of the presently claimed substances in vivo according to a standard test method involving murine lymphocytic leukemia P-388 is presented to lend further assurance as to the utility of the compounds as inhibitors of mammalian tumors.

Lymphocytic leukemia P-388 cells ($1 \times 10^5/0.2$ ml) were transplanted intraperitoneally into male BDF$_1$-SLC mice (5 mice/group). Each of the compounds of this invention was diluted with physiological saline to various concentrations. Each dilution was administered at a dose of 0.1 ml/10 g of body weight once daily for 9 days, starting on the day after the day of the transplantation. The mice of the control group were administered physiological saline.

The mice were observed for 30 days, beginning on the day after the day of P-388 transplantation, to examine how many days each mouse survived. The average numnber of days that the group receiving the compound of this invention survived was calculated. The figure obtained was divided by the average number of survival days for the control group, and was multiplied by 100 (T/C (%)).

T/C value more than 130 was considered to be effective.

The results are shown in Table 11.

TABLE 11

Max. T/C on Mouse Lymphocytic Leukemia P 388

| Compound | Max. T/C | Compound | Max. T/C |
|---|---|---|---|
| 15 MDBZOBZ | 165 | 37 EEDBZ | 168 |
| 21 MANTR | 148 | 38 BBDBZ | 156 |
| 22 MCO | 174 | 39 MTBZ | 163 |
| 23 MDBZME | 130 | 40 ATBZ | 154 |
| 27 MDBZ | 149 | 41 PPDBZ | 184 |
| 32 MCU | 166 | 42 PPCO | 177 |
| 34 MDDBZOBZ | 205 | 43 PYDBZ | 182 |
| 35 MMDBZ | 153 | 45 PYCO | 163 |
| 36 MMCO | 150 | 46 EECLPE | 150 |

(4) Acute toxicity

LD$_{50}$ was assayed by administering several representative compounds of this invention for 10 consecutive days.

1. Method of experiment.

CDF$_1$/SLC strain male mice (each 6 weeks old, 7 members per group) were subcutaneously administered with various compounds of this invention, the dose being different with each compound. LD$_{50}$ (daily dose) was estimated from the mortality during the administration period by the Behrens-Kärber method.

2. Results of experiment.

The results were as shown in Table 5.

TABLE 5

| No. | Compound Abbreviation | LD$_{50}$ (mg/kg/day) |
|---|---|---|
| 32 | MCU | 17.5 |
| 34 | MDDBZOBZ | 60.0 |
| 37 | EEDBZ | 50.0 |
| 43 | PYDBZ | 12.5 |
| Bleomycin complex | | 20 |

As is apparent from their biological properties described above, the compounds of this invention have antimicrobial activity several fold greater than that of bleomycin, Hela S cell inhibitory activity in vitro, and P 388 cell inhibitory activity in vivo, and are greatly reduced in side effects such as pulmonary toxicity relative to bleomycin. They are administered to a mammal bearing a tumor in a substantially non-toxic antitumor effective amount. Activity may be demonstrated in experimental animal tumors. The compounds can be administered in various dosage forms such as, for example, solid preparation, ointment, and solutions but generally in the form of injections. The total dose is from 5 to 200 per week, which may be divided into from 1 to 5 portions.

The compounds are basic and form salts with acids as is known for bleomycin. The preferred salts for pharmaceutical use are those which are pharmaceutically acceptable. These are the salts having an anion which does not contribute appreciably to toxicity such as chloride, phosphate, sulfate, etc. and the anions of various non-toxic organic carboxylic and sulfonic acids such as methanesulfonate, acetate, and proprionate.

The expression "lower" when used to modify a term such as "alkyl", "alkylene", "alkoxy", is intended to refer to such groups having 1 to 6 carbon atoms.

The invention is illustrated below in detail with reference to Examples, but not limited thereto.

EXAMPLE 1

Step A:

To a solution of 1.0 g of 3-[N-methyl-N-(3-aminopropyl)amino]propylaminobleomycin trihydrochloride (Cu-containing form) in 30 ml of methanol, was added 227 mg of cycloundecane carboxaldehyde followed by 26 mg of sodium cyanoborohydride. The mixture was allowed to react at room temperature for 16 hours. The reaction mixture was adjusted to pH 1.0 with 6N hydrochloric acid and left standing for 10 minutes to terminate the reaction. The reaction mixture was then neutralized with 1N sodium hydroxide solution and freed from the methanol by distillation under reduced pressure. The residue was made up to 50 ml with distilled water and extracted with ether to remove the excess aldehyde. The aqueous layer was passed through a column, 100 ml in volume, packed with Amberlite ®XAD-2 (Rohm and Haas Co.) in 4-% aqueous ammonium acetate solution —2-% aqueous acetic acid solution (1:1 v/v) to adsorb the intended product. The adsorbed phase was eluted by the linear concentration gradient technique using 500 ml of the said buffer solution to which was continuously added 500 ml of methanol. The fractions, 200 ml in total, which had been eluted at methanol concentrations of about 65% and showed absorption maxima at wave lengths of about 290 mµ were collected. The aqueous solution obtained from these fractions after removing the methanol by distillation under reduced pressure was passed through a column, 100 ml in volume, packed with Amberlite ®XAD-2 (Rohm and Haas Co.) in distilled water, to adsorb the intended product. The column was washed with 150 ml of distilled water and the intended product was eluted with 1/50M aqueous hydrochloric acid-methanol (1:4 v/v). Blue fractions of the bleomycin derivative were collected, neutralized with Dowex ®44 (an anion exchange resin, OH-type, of Dow Chemical Co.), then concentrated under reduced pressure, and lyophilized.

The lyophilized powder obtained above was dissolved in 10 ml of distilled water and passed through a column, 100 ml in volume, packed with CM-Sephadex ®C-25 (Na+-type, Pharmacia Fine Chemicals Co.), which had been equilibrated with 1/20M acetic acid-sodium acetate buffer of pH 4.5, to effect adsorption onto the column. The intended product was eluted by the linear concentration gradient technique which was carried out by continuously adding sodium chloride to the said buffer solution to increase gradually the concentration of sodium chloride to 1.0M. A total of 550 ml of the eluent was allowed to flow through the column and 120 ml in total of the blue fractions eluted at sodium chloride concentrations of about 0.65M were collected. The collected fractions were desalted with Amberlite ®XAD-2, which was employed above, and lyophilized to yield 872 mg (79% yield) of copper-containing 3-{N-methyl-N-[3'-(cycloundecanylmethylamino)propyl]amino}propylaminobleomycin in blue amorphous powder form.

Step B:

The copper-containing product, 872 mg, obtained in Step A was dissolved in 18 ml of distilled water. For the purpose of copper removal, the resulting solution was passed through a column, 100 ml in volume, packed with Amberlite ®XAD-2 in distilled water, to effect adsorption, and the resin was washed with 300 ml of an aqueous solution containing sodium chloride and 5% EDTA.2Na, then successively with 100 ml of 2% sodium chloride solution and 150 ml of distilled water, and finally the adsorbed phase was eluted with 1/50N aqueous hydrochloric acid-methanol (1:4 v/v) to collect the eluate fractions which showed absorption maxima at wave lengths of about 290 mµ. The collected fractions were adjusted to pH 60 with Dowex ®44 (OH-type, Dow Chemical Co.), concentrated under reduced pressure and lyophilized to give 758 mg (90% yield) of a white amorphous powder of 3-{N-methyl-N-[3'-(cycloundecanylmethylamino)propyl]amino}propylaminobleomycin (Compound No. 32) in the form of copper-free trihydrochloride. This compound showed UV absorption maximum at 291 mµ and E (1%/1 cm)=87, as measured in distilled water. The IR absorption maxima (in wave number, cm$^{-1}$), as measured in KBr-tablet, were: 3425, 2950, 1650, 1550, 1520, 1440, 1400, 1260, 1190, 1140, 1100, 1060, 1020, 980, and 800. Other physicochemical properties were as shown in Table 2.

In the above reaction, 938 mg of m,p-dibenzyloxybenzaldehyde was used as the aldehyde component and the reaction was carried out at 27° C. for 70 hours. The reaction mixture was purified and removed of copper in a similar manner to that described above to obtain 762 mg (57% yield) of a colorless amorphous powder of 3-{N-methyl-N-[3'-(bis(m,p-dibenzyloxybenzyl)amino)-propyl]amino}propylaminobleomycin (Compound No. 34) in the form of copper-free trihydrochloride. This compound showed UV absorption maximum at 285 mµ and E (1%/1 cm)=86, as measured in distilled water. The IR absorption maxima (in wave number, cm$^{-1}$), as measured in KBr-tablet, were: 3425, 2950, 1650, 1550, 1510, 1460, 1430, 1380, 1320, 1270, 1190, 1140, 1060, 1020, 960, 800, 730, 690, and 650.

Similarly, 174 mg of cyclooctanecarboxaldehyde was used as an aldehyde and allowed to react at room temperature for 24 hours, then purified and removed of copper to obtain 605 mg (58% yield) of a colorless amorphous powder of 3-{N-methyl-N-[3'-(cyclooctylmethylamino)propyl]amino}propylaminobleomycin (Compound No. 22) in copper-free trihydrochloride form. This compound showed UV absorption maximum at 291 mµ and E (1%/1 cm)=86, as measured in distilled water. The IR absorption maxima (in wave number, cm$^{-1}$), as measured in KBr-tablet, were: 3425, 2925, 1650, 1550, 1520, 1440, 1400, 1330, 1260, 1190, 1140, 1100, 1060, 1020, 980, and 800.

In a similar manner, the compounds shown in Table 6 were prepared.

hyde and the reaction mixture was purified and removed of copper to yield 587 mg (55% yield) of a copper-free colorless amorphous powder of 3-{N,N-dimethyl-N-[3'-(N,N-dimethyl-N-(3'-dibenzylaminopropyl)amino)propyl]amino}propylaminobleomycin

TABLE 6

| Intended Compound No. | Starting Compound (formula III) | Number of equivalents of compound III | Reaction time (hour) | Reaction temp. (°C.) | Yield (%) |
|---|---|---|---|---|---|
| 1 | p-Chlorophenylacetaldehyde | 1.2 | 16 | 22 | 66 |
| 7 | m,p-Dichlorobenzaldehyde | 1.2 | 16 | 22 | 77 |
| 8 | o,p-Dichlorobenzaldehyde | 1.2 | 16 | 22 | 71 |
| 13 | o,p-Dimethoxybenzaldehyde | 1.2 | 16 | 22 | 58 |
| 14 | p-Chloroacetophenone | 2.0 | 24 | 37 | 57 |
| 15 | m,p-Dibenzyloxybenzaldehyde | 1.2 | 18 | 22 | 63 |
| 17 | Diphenylacetaldehyde | 1.2 | 16 | 22 | 67 |
| 18 | p-Cyanobenzaldehyde | 1.2 | 16 | 22 | 83 |
| 21 | Anthracene-9-aldehyde | 1.2 | 18 | 22 | 61 |
| 22 | Cyclooctanecarbaldehyde | 2.0 | 24 | 37 | 58 |
| 27 | Benzaldehyde | 10.0 | 16 | 22 | 67 |
| 28 | Cyclopentanecarbaldehyde | 1.2 | 16 | 22 | 61 |
| 29 | Cyclohexanecarbaldehyde | 1.2 | 16 | 22 | 60 |
| 30 | 2-Cyclohexylacetaldehyde | 1.2 | 16 | 22 | 54 |
| 31 | Cycloheptylcarbaldehyde | 1.2 | 16 | 22 | 74 |
| 32 | Cycloundecanecarbaldehyde | 2.0 | 16 | 22 | 71 |
| 34 | m,p-Dibenzyloxybenzaldehyde | 5.0 | 70 | 27 | 57 |
| 47 | Cyclotridecanecarbaldehyde | 2.0 | 16 | 22 | 66 |
| 48 | 3,4-Di(p-chlorobenzyloxy)benzaldehyde | 4.0 | 96 | 27 | 54 |
| 49 | 3,4-Di(m,p-dichlorobenzyloxy)benzaldehyde | 4.0 | 120 | 40 | 44 |
| 50 | 3,4-Di(p-methoxybenzyloxy)benzaldehyde | 4.0 | 24 | 40 | 49 |
| 51 | 4-(p-Benzyloxybenzyloxy)benzaldehyde | 4.0 | 24 | 40 | 41 |
| 52 | p-Cyclooctylmethyloxybenzaldehyde | 4.0 | 48 | 40 | 33 |
| 53 | 3,4,5-Tribenzyloxybenzaldehyde | 4.0 | 24 | 40 | 44 |

EXAMPLE 2

Step A:

To a solution of 1.0 g of 3-[N,N-diethyl-N-(3-aminopropyl)]aminopropylaminobleomycin trichloride (Cu-containing form) in 30 ml of methanol, was added 642 mg of benzaldehyde followed by 51 mg of sodium cyanoborohydride. The mixture was allowed to react at room temperature for 16 hours. In a manner similar to that in Example 1, the reaction mixture was treated with hydrochloric acid, extracted with ether, subjected to the Amberlite ®XAD-2 column chromatography, then desalted by using Amberlite ®XAD-2 as described previously, and lyophilized to yield 832 mg (75% yield) of copper-containing 3-[N,N-diethyl-N-(3'-dibenzylamino)propyl]aminopropylaminobleomycin in blue amorphous powder form.

Step B:

The copper-containing product, 832 mg in weight, obtained in Step A was dissolved in 17 ml of distilled water, then removed of the copper as in Step B of Example 1, concentrated under reduced pressure, and lyophilized to yield 739 mg (92% yield) of a copper-free white amorphous powder of 3-[N,N-diethyl-N-(3'-dibenzylamino)propyl]aminopropylaminobleomycin (Compound No. 37) trihydrochloride. It showed UV absorption maximum at 291 mμ and E (1%/1 cm)=90, as measured in distilled water. The IR absorption maxima (in wave number, cm$^{-1}$), as measured in KBr-tablet, were: 3425, 2975, 2925, 1640, 1550, 1520, 1490, 1450, 1400, 1320, 1260, 1190, 1140, 1100, 1060, 1020, 980, 910, 800, 740, and 690.

In a similar manner to that described above, 1.0 g of 3-{N,N-dimethyl-N-[3'-(N,N-dimethyl-N-(3'-aminopropylamino)propyl]amino}propylaminobleomycin tetrahydrochloride (Cu-containing form), used as starting material, was allowed to react with 607 mg of benzaldehyde and the reaction mixture was purified and removed of copper to yield 587 mg (55% yield) of a copper-free colorless amorphous powder of 3-{N,N-dimethyl-N-[3'-(N,N-dimethyl-N-(3'-dibenzylaminopropyl)amino)propyl]amino}propylaminobleomycin (Compound No. 41) tetrahydrochloride. It showed UV absorption maximum at 291 mμ and E (1%/1 cm)=84, as measured in distilled water. The IR absorption maxima (in wave number, cm$^{-1}$), as measured in KBr-tablet, were: 3425, 2950, 1650, 1560, 1490, 1460, 1400, 1330, 1260, 1190, 1160, 1100, 1060, 1020, 980, 800, 740, and 600.

A reaction was carried out in the same manner as above by using 161 mg of cyclooctanecarbaldehyde in place of the benzaldehyde and the reaction mixture was similarly purified and removed of copper to yield 539 mg (52% yield) of a copper-free colorless amorphous powder of 3-{N,N-dimethyl-N-[3'-(N,N-dimethyl-N-(3''-cyclooctylmethylaminopropylamino)propyl]amino}propylaminobleomycin (Compound No. 42) tetrahydrochloride. It showed UV absorption maximum at 291 mμ and E (1%/1 cm)=87, as measured in distilled water. The IR absorption maxima (in wave number, cm$^{-1}$), as measured in KBr-tablet, were: 3425, 2950, 1720, 1660, 1550, 1520, 1490, 1450, 1400, 1360, 1260, 1190, 1140, 1100, 1060, 1020, 980, 880, and 800.

In a similar manner, 1.0 g of 3-[4-(3-aminopropyl)piperazin-1-yl]propylaminobleomycin tetrahydrochloride (Cu-containing form), used as starting material, was allowed to react with 623 mg of benzaldehyde and the reaction mixture was purified and removed of copper to yield 695 mg (65% yield) of a copper-free colorless amorphous powder of 3-[4-(3-dibenzylaminopropyl)-piperazin-1-yl]propylaminobleomycin (Compound No. 43) tetrahydrochloride. It showed UV absorption maximum at 291 mμ and E (1%/1 cm)=93. The IR absorption maxima (in wave number, cm$^{-1}$), as measured in KBr-tablet were: 3425, 2950, 1660, 1560, 1520, 1550, 1460, 1260, 1190, 1140, 1100, 1060, 1030, 980, 880, 810, 740, and 700.

Similarly, compounds shown in Table 7 were prepared.

TABLE 7

| Intended compound No. | Abbreviation | Abbreviation for compound of formula II | Compound of formula III | Number of equivalent of compound III | Reaction time (hour) | Yield (%) |
|---|---|---|---|---|---|---|
| 35 | MMDBZ | MMHH | Benzaldehyde | 10.0 | 16 | 72 |
| 36 | MMCO | MMHH | Cyclooctanecarbaldehyde | 2.0 | 24 | 57 |
| 37 | EEDBZ | EEHH | Benzaldehyde | 10.0 | 16 | 69 |
| 38 | BBDBZ | BBHH | Benzaldehyde | 10.0 | 16 | 68 |
| 39 | MTBZ | MBZHH | Benzaldehyde | 15.0 | 16 | 68 |
| 40 | ATBZ | APP | Benzaldehyde | 15.0 | 20 | 65 |
| 41 | PPDBZ | PP4M | Benzaldehyde | 10.0 | 16 | 55 |
| 42 | PPCO | PP4M | Cyclooctanecarbaldehyde | 2.0 | 24 | 52 |
| 43 | PYDBZ | PY | Benzaldehyde | 10.0 | 16 | 65 |
| 44 | PYCLBZ | PY | p-Chlorobenzaldehyde | 1.2 | 16 | 48 |
| 45 | PYCO | PY | Cyclooctanecarbaldehyde | 2.0 | 24 | 43 |
| 46 | EECLPE | EEHH | p-Chlorophenylacetaldehyde | 1.3 | 16 | 41 |

EXAMPLE 3

Into 300 ml of distilled water, were suspended 50 g of 3-aminopropyldimethylamine and 62 g of sodium hydrogencarbonate. To the suspension, while cooling in ice and stirring vigorously, was added dropwise 105 g (1.5 equivalents) of benzoyl chloride. After 6 hours of reaction at room temperature, the reaction mixture was acidified to pH 4 with concentrated hydrochloric acid and extracted with ethyl ether to remove the excess benzoyl chloride. The aqueous layer was adjusted to pH 12 with 5N aqueous sodium hydroxide solution and extracted with chloroform. The chloroform extract was dried over sodium sulfate and stripped of the solvent by distillation under reduced pressure to give 91 g of 3-benzamidopropyldimethylamine. To this residue, was added a solution of 118 g (1 equivalent) of N-3-bromopropylphthalimide in 300 ml of tetrahydrofuran. After stirring at room temperature for 18 hours, the precipitated colorless crystals were collected by filtration, washed with tetrahydrofuran and dried to yield 188 g (90% yield) of colorless crystals of the quaternary ammonium salt. This salt was dissolved in 1,000 mg of 6N hydrochloric acid and heated at 110° C. for 8 hours to effect hydrolysis. After cooling, the precipitated phthalic and benzoic acids were removed by filtration and the filtrate was evaporated to dryness under reduced pressure to remove the excess hydrochloric acid. The residue was dissolved in distilled water and passed through a column of an ion exchange resin Dowex ®-1 (Cl-type, 600 ml in volume). The effluent was evaporated to dryness under reduced pressure to yield 96 g (90% yield) of bis(3-aminopropyl)dimethylammonium trihydrochloride. This compound was too hygroscopic to determine its melting point. The PMR spectrum measured in heavy water showed the following δ values: 2.1–2.8 ppm, 4H (m), 2.4 ppm, 6H (s), 3.1–3.9 ppm, 8H (m) (wherein, the letters in parentheses indicate the signal types: m: multiplet, s: singlet). These values were in compliance with the assigned structure. The IR absorption maxima (in wave number, $cm^{-1}$), as measured in KBr-tablet, were: 3425, 2975, 2625, 2000, 1600, 1480, 1470, 1350, 1320, 1300, 1230, 1200, 1160, 1140, 1060, 1040, 1000, 930, 840, and 760.

In a similar manner to that described above, using 3-aminopropyldiethylamine and 3-aminopropyldibutylamine, there were obtained bis(3-aminopropyl)-diethylammonium trihydrochloride and bis(3-aminopropyl)dibutylammonium trihydrochloride, respectively. The physicochemical properties of these compounds were as shown in Table 8.

TABLE 8

| Synthesized amine | IR ($cm^{-1}$), KBr-tablet | *1 PMR (ppm) 60 MHz, D20 | | *2 $R_m$ | *3 $R_f$ |
|---|---|---|---|---|---|
| bis(3-Aminopropyl)-dimethylammonium trihydrochloride | 3425, 2975, 2625, 2000, 1600, 1480, 1470, 1350, 1320, 1300, 1230, 1200, 1160, 1140, 1060, 1040, 1000, 930, 840, 760 | 2.1~2.8<br>3.1~3.9<br>2.4 | 4H (m)<br>8H (m)<br>6H (s) | 2.63 | 0.08 |
| bis(3-Aminopropyl)-diethylammonium trihydrochloride | 3425, 2975, 2500, 2000, 1600, 1480, 1400, 1280, 1180, 1060, 1000, 950, 900, 880, 800, 750 | 1.6<br>2.0~2.7<br>3.1~4.0 | 6H (t)<br>4H (m)<br>12H (m) | 2.43 | 0.14 |
| bis(3-Aminopropyl)-dibutylammonium trihydrochloride | 3425, 2975, 2650, 2000, 1600, 1470, 1400, 1390, 1350, 1280, 1260, 1180, 1070, 1030, 990, 950, 900, 840, 800, 750 | 1.15<br>1.3~2.2<br>2.0~2.7<br>3.1~4.0 | 3H (t)<br>8H (m)<br>4H (m)<br>12H (m) | 1.89 | 0.44 |

NOTE:
*1 Letters in parentheses: s stands for singlet, t for triplet, and m for multiplet.
*2 Rate of electrophoresis relative to alamine ($R_m$ = 1.0) in thin-layer electrophoresis [Avicel ® SF (FMC Co.); formic acid-acetic acid-water (25:75:900 v/v); 800 v; 6 minutes].
*3 Mobility in thin-layer chromatography [silica gel 60 F. 25.4 (Merck Co.); methanol-10% aqueous ammonium acetate-10% aqueous ammonia (1:1:1 v/v);

EXAMPLE 4

To a solution of 53.6 g (2 equivalents) of N-(bromopropyl)phthalimide in 300 ml of acetonitrile, was added 13 g of N,N,N',N'-tetramethyl-1,3-diaminopropane. The mixture was stirred at room temperature for 18 hours to form 1,3-[(3-phthalimidopropyl)dimethylamino]propane dibromide as a white precipitate. The precipitate was collected by filtration, washed with acetonitrile, and dried. The yield was 90%. This quaternary ammonium salt was dissolved in 200 ml of 6N hydrochloric acid and heated at 110° C. for 8 hours to effect hydrolysis. After cooling, the precipitated phthalic acid was removed by filtration. The filtrate was passed through a column of an ion exchange resin Dowex®-1 (Cl-type; 1200 ml in volume). The effluent was evaporated to dryness under reduced pressure to yield 28.7 g of 1,3-bis[(3-aminopropyl)dimethylamino]-propane tetrahydrochloride.

This compound was too hygroscopic to determine the melting point. The PMR spectrum, as measured in heavy water, showed the following δ(ppm) values: 2.0–2.9, 6H (m); 3.0–4.0, 12H (m); 3.45, 12H (s). The letters in parentheses have the same meanings as described previously The δ values indicate the structure of the compound given above. The values of $R_f$ and $R_m$, as determined under the conditions given in the note of Table 8, were 0.02 and 2.56, respectively. The IR absorption maxima (in wave numbers, $cm^{-1}$) as measured in KBr-tablet, were: 3425, 2975, 2600, 2000, 1720, 1600, 1480, 1470, 1400, 1300, 1230, 1200, 1150, 1060, 1000, 960, 920, 900, 850, and 760.

EXAMPLE 5

To a solution of 20 g of N-methylbenzylamine in 300 ml of tetrahydrofuran, were added 17 g of triethylamine and 89 g of N-(3-bromopropyl)phthalimide. The mixture was stirred at room temperature for 17 hours. The colorless precipitate which was separated out was collected by filtration and recrystallized from aqueous ethanol to yield 76 g (80% yield) of colorless crystals. The crystals were dissolved in 380 ml of 6N hydrochloric acid, and heated at 110° C. for 8 hours, and then cooled, removed of the precipitated phthalic acid by filtration, concentrated under reduced pressure to remove the excess hydrogen chloride, dissolved in distilled water, and passed through a column of an ion exchange resin, Dowex®-1 (Cl-type, 200 ml in volume). The effluent was evaporated to dryness under reduced pressure to yield 41 g (90% yield) of bis(3-aminopropyl)methylbenzylammonium trihydrochloride. This compound was too hygroscopic to determine its melting point. The PMR spectrum, as measured in heavy water, showed the following δ(ppm) values: 1.9–2.8, 4H (m); 2.9–4.0, 8H (m); 3.2, 3H (s); 4.70–4.75, 2H (m); 7.7, 5H (s); the letters in parentheses are as defined above. Those values indicate the structure of the above-mentioned compound. The values of $R_f$ and $R_m$ determined under the condititons given in Table 8 were 0.29 and 2.14, respectively. The IR absorption maxima (in wave number, $cm^{-1}$), as measured in KBr-tablet, were as follows: 3425, 2975, 2650, 2000, 1600, 1470, 1400, 1310, 1220, 1180, 1140, 1070, 1030, 1000, 960, 890, 780, 750, 730, and 700.

REFERENCE EXAMPLE 1

Into 10 ml of dimethylformamide, were dissolved 1,000 mg of bleomycin acid (Cu-chelate) and 2,948 mg of 1-hydroxybenztriazole (briefly HOBT). To the solution, while being cooled at 0° C. and stirred, was added 1,500 mg (10 equivalent to bleomycinic acid) of dicyclohexylcarbodiimide (briefly DCC). Ten minutes thereafter, to the mixture was added a solution of 1,953 mg (10 equivalent to bleomycin) of N-(3-aminopropyl)-N,N-dimethylaminopropylamine trihydrochloride, which had been separately prepared, and 2,206 mg (30 equivalent to bleomycin) of N-methylmorpholine in 5 ml of dimethylformamide. The mixture was allowed to react with stirring at room temperature for 4 hours. To the reaction mixture, was added acetone (10 times the volume of reaction mixture) to precipitate the intended product. The precipitate was washed thoroughly with acetone, dissolved in distilled water, and passed through a column, 100 ml in volume, packed with CM-Sephadex®C-25 ($Na^+$ type, Pharmacia Fine Chemicals Co.), which had been equilibrated with a 1/20M acetic acid-sodium acetate buffer solution (pH 4.5), to effect adsorption. The adsorbed phase was eluted by the linear concentration gradient technique which was carried by continuously adding sodium chloride to the above buffer solution to increase the sodium chloride concentration gradually to 1.0M. The blue fractions eluted at about 0.45M were collected, desalted by using Amberlite®XAD-2, as described previously, and lyophilized to yield 624 mg of Cu-containing 3-[N-(3-aminopropyl)-N,N-dimethyl]aminopropylaminobleomycin in the form of blue amorphous powder. The UV absorption maxima, as measured in distilled water, were at 292 mµ and 243 mµ and E (1%/1 cm)=124 and 155, respectively. The IR absorption maxima (in wave number, $cm^{-1}$), as measured in KBr-tablet, were 3425, 2975, 2925, 1720, 1640, 1560, 1460, 1400, 1370, 1330, 1300, 1250, 1200, 1140, 1100, 1060, 1010, 990, 930, 880, and 760. Other physicochemical properties were as shown in Table 9.

In a similar manner to that described above, the compounds shown in Table 9 were synthesized.

TABLE 9

| Synthesized compound of formula II (abbreviation) | Amine used as starting material, compound of formula IV | UV absorption maximum of Cu—containing product, mµ, (E 1%/1 cm) | TLC of Cu—containing product, $R_f$*1 | Electrophoresis of Cu—containing product, $R_m$ *2 |
|---|---|---|---|---|
| MMHH | bis(3-Aminopropyl)dimethyl-ammonium salt | 292 (124) 243 (155) | 0.81 | 1.10 |
| EEHH | bis(3-Aminopropyl)diethyl-ammonium salt | 292 (116) 243 (145) | 0.82 | 1.06 |
| BBHH | bis(3-Aminopropyl)dibutyl-ammonium salt | 292 (112) 243 (139) | 0.73 | 1.04 |
| PP4M | bis(3-Aminopropyl)methylbenzyl-ammonium salt | 292 (111) 243 (138) | 0.42 | 1.15 |
| MBZHH | 1,3-[bis(3-Aminopropyl)dimethyl-amino]propane | 292 (123) 244 (152) | 0.70 | 1.03 |

NOTE:
*1: Silica gel 60 F 254 silanised ® (Merck Co.); methanol-6% ammonium acetate (45:55 v/v)
*2: Avicel SF ® (FMC Co.); formic acid-acetic acid-water (25:75:900); 800 v; 15 minutes.

REFERENCE EXAMPLE 2

Synthesis of 3,4-di-(3',4'-dichlorobenzyloxy)benzaldehyde

To a solution of 2 g of 3,4-dihydroxybenzaldehyde in 40 ml of acetone, were added 4.40 g of anhydrous potassium carbonate and 6.24 g of 3,4-dichlorobenzyl bromide. The mixture was refluxed for 24 hours. The reaction mixture was then removed of the acetone by distillation under reduced pressure, admixed with 200 ml of water, and the intended product was extracted with 200 ml of chloroform. The chloroform layer was dried over anhydrous sodium sulfate, and stripped of the chloroform by distillation under reduced pressure to precipitate white crystals. The raw crystals were recrystallized from ethyl alcohol to give 4.99 g of colorless crystals having a melting point of 181°–183° C. The IR absorption spectrum of the compound, as measured in KBr-tablet, showed the following absorption maxima (in wave number, cm$^{-1}$) 658, 693, 710, 760, 795, 805, 830, 875, 1030, 1135, 1168, 1200, 1245, 1280, 1370, 1403, 1437, 1460, 1470, 1510, 1585, 1600, 1690, 2730, 2830, 2870, 2910, and 3070.

The NMR spectrum, as measured in deuterochloroform, showed the following signals: 5.20 (s) 2H; 6.93–7.67 (m) 9H; 5.23 (s) 2H; 9.87 (s) 1H.

In a manner similar to that described above, the compounds shown in Table 10 were obtained.

methylenecyclotridecane. To a solution of this substance in 40 ml of anhydrous dichloromethane, after having been cooled to −15° C., was added dropwise with stirring a solution of 2.64 g of m-chloroperbenzoic acid in 40 ml of anhydrous dichloromethane. After 3 hours of reaction, the organic layer was washed successively with 10-% sodium sulfite solution, 7-% sodium hydrogencarbonate solution, and saturated sodium chloride solution, then dried and concentrated under reduced pressure. The residue was purified by the silica gel chromatography [developed with a petroleum ether-ethyl acetate (20:1) mixture] to yield 2.04 g (95% yield based on the ketone compound) of an epoxide. To a solution of the epoxide in anhydrous dichloromethane, after having been cooled to −18° C., was added dropwise a borontrifluoride-ether complex. After completion of the addition, water was added to the reaction mixture. The organic layer was separated, then concentrated, and purified by the silica gel chromatography to yield only cyclotridecanecarbaldehyde in a yield of 60–70%.

The IR absorption spectrum of the compound, as measured in KBr-tablet, showed the following absorption maxima at 723, 735, 825, 970, 1070, 1110, 1128, 1196, 1220, 1255, 1285, 1350, 1420, 1450, 1465, 1590, 1710, 1735, 2700, 2870, and 2920.

The NMR spectrum, as measured in deutorochloroform, showed the following signals:

TABLE 10

| Formula IX | | Intended product (formula X) | | |
|---|---|---|---|---|
| Starting Compound Formula VIII | Name | Melting point, °C. | IR | NMR |
| 3,4-Dihydroxybenzaldehyde p-Chlorobenzyl bromide | 3,4-di-(p-Chloro-benzyloxy)benzaldehyde | 108–110 | 660, 680, 755, 800, 835, 848, 870, 1013, 1033, 1090, 1135, 1168, 1208, 1236, 1270, 1350, 1380, 1407, 1437, 1456, 1493, 1510, 1575, 1585, 1600, 1685, 1900, 2740, 2870, 2910, 3070 | 5.16 (s) 2H, 5.20 (s) 2H, 6.9–7.6 (m) 11H, 9.82 (s) 1H |
| 3,4-dihydroxybenzaldehyde p-Methoxybenzyl chloride | 3,4-di-(p-Methoxy-benzyloxy)benzaldehyde | Oily Substance | 750, 764, 790, 820, 860, 875, 935, 960, 985, 1000, 1028, 1118, 1170, 1187, 1235, 1255, 1270, 1310, 1340, 1390, 1430, 1465, 1520, 1590, 1620, 1700, 2740, 2850, 2880, 2950, 3030 | 3.88 (s) 6H, 5.18 (s) 2H, 5.22 (s) 2H, 6.83–7.6 (m) 11H, 9.84 (s) 1H |
| 4-Hydroxybenzaldehyde 4-Benzyloxybenzyl chloride | 4-(4-Benzyyloxybenzyl-oxy)benzaldehyde | 102–104 | 690, 725, 795, 810, 845, 875, 995, 1030, 1035, 1115, 1165, 1180, 1215, 1245, 1260, 1305, 1315, 1385, 1425, 1453, 1515, 1575, 1603, 1695, 1895, 2750, 2810, 2830, 2875, 2910, 2950, 3050, 3075 | 5.07 (s) 4H, 6.85–7.93 (m) 13H, 9.83 (s) 1H |
| 4-Hydroxybenzaldehyde Cyclooctylmethyl bromide | 4-(Cyclooctylmethoxy)-benzaldehyde | Oily Substance | 830, 860, 1010, 1033, 1110, 1160, 1215, 1255, 1313, 1360, 1393, 1425, 1445, 1465, 1600, 1692, 1710, 1787, 2740, 2855, 2920 | 1.6 (br, s) 15H, 3.78 (d, J = 1.1 HZ) 2H, 6.96, 7.80 (A$_2$B$_2$, J = 1.4 HZ), 9.86 (s) 1H |

REFERENCE EXAMPLE 3

Preparation of cyclotridecanecarbaldehyde

To a stirred mixture of 3 g of zinc dust, 50 ml of anhydrous tetrahydrofuran and 2.66 g of dibromomethane, was added dropwise a solution of 2.13 g of anhydrous titanium tetrachloride in 5 ml of dichloromethane. After 15 minutes, to the resulting solution was added dropwise a solution of 2 g of cyclotridecanone in 8 ml of anhydrous tetrahydrofuran. The mixture was allowed to react at room temperature for 12 hours. The reaction mixture was diluted with 50 ml of pentane, admixed with 100 ml of 1-M hydrochloric acid, and intermixed by shaking. The organic layer was washed successively with water, dilute aqueous sodium hydrogencarbonate solution, and saturated aqueous sodium chloride solution, then dried, and concentrated to yield NMR: 1.39 (br,s), 24H, (—CH$_2$—×12), 2.1∼2.5 (m), 1H, (—C$\underline{H}$—), 9.58 (d, J=1.5 $\overline{HZ}$), 1H, (1—C$\underline{H}$O).

What is claimed:

1. An aminopropylaminobleomycin represented by the following general formula or a salt thereof:

[BX]—NH—(CH$_2$)$_3$—A—(CH$_2$)$_3$—B wherein

[BX] represents the bleomycin acid acyl group;

A is

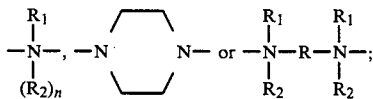

$R_1$ and $R_2$ are independently lower alkyl or benzyl;
R is lower alkylene;
n is the integer 0 or 1; and
B has the formula

wherein
(i) $R_3$ is hydrogen and $R_4$ is
  (a) benzyl substituted by one or more halogen atoms, provided that the benzyl is substituted by two halogen atoms when $R_1$ is lower alkyl,
  (b) benzyl substituted by cyano, two or more alkoxy groups or two or more benzyloxy groups,
  (c) lower alkyl substituted by cycloalkyl or anthranyl,
  (d) phenylethyl substituted by one or more halogen atoms, or
  (e) diphenylethyl; or
(ii) both $R_3$ and $R_4$ are benzyl which may be substituted by one or more
  (a) benzyloxy groups,
  (b) ring substituted benzyloxy groups in which the ring substituents may be one or more halogen atoms, lower alkoxy groups or benzyloxy groups, or
  (c) cycloalkylmethoxy groups;

2. An aminopropylaminobleomycin or a salt thereof according to claim 1, wherein

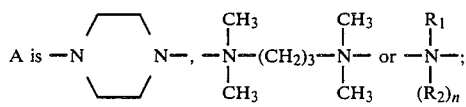

$R_1$ is lower alkyl;
$R_2$ is a lower alkyl or benzyl;
n is the integer 0 or 1; and
(i) $R_3$ is hydrogen and $R_4$ is
  (a) benzyl substituted by one or more halogen atoms, provided that the benzyl is substituted by two halogens when $R_1$ is lower alkyl,
  (b) benzyl substituted by cyano, two or more $C_1$–$C_4$ alkoxy groups or two or more benzyloxy groups,
  (c) methyl substituted by a $C_8$–$C_{13}$ cycloalkyl group, or
  (d) diphenylmethyl; or
(ii) both $R_3$ and $R_4$ are benzyl optionally substituted by one or more
  (a) benzyloxy groups which may contain one or more ring substituents selected from halogen atoms, $C_1$–$C_4$ alkoxy or benzyloxy, or
  (b) $C_8$–$C_{13}$ cycloalkylmethoxy groups.

3. An aminopropylaminobleomycin or a salt thereof according to claim 1, wherein
A is

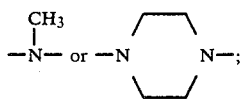

$R_3$ is benzyl, substituted benzyl having one or more substituents selected from benzyloxy, cycloalkylmethyl having 11 to 13 carbon atoms in the cycloalkyl group, and
$R_4$ is a hydrogen atom, a benzyl group, or a benzyl group substituted by one or more benzyloxy groups.

4. The compound of claim 1 which is 3-{N-Methyl-N-[3'-(cycloundecanylmethylamino)propyl]amino}propylaminobleomycin.

5. The compound of claim 1 which is 3-{N-Methyl-N-[3'-(bis(m,p-dibenzyloxybenzyl)amino)priopyl]amino}propylaminobleomycin.

6. The compound of claim 1 which is 3-[4'-(3''-dibenzylaminopropyl)piperazin-1-yl]propylaminobleomycin.

7. The compound of claim 1 which is 3-{N,N-dimethyl-N-[3'-(dibenzylamino)propyl]amino}propylaminobleomycin.

8. The compound of claim 1 which is 3-{N,N-dimethyl-N-[3'-(N,N-dimethyl-N-(3''-dibenzylaminopropyl)amino)propyl]amino}propylaminobleomycin.

9. The compound of claim 1 which is 3-{N,N-dimethyl-N-[3'-(N,N-dimethyl-N-(3''-cyclooctylmethylaminopropyl)amino)propyl]amino}propylaminobleomycin.

10. The method for inhibiting an experimental mammalian tumor which comprises systemically administering to a mammal bearing a tumor a non-toxic anti-tumor effective amount of a Compound of claim 1.

* * * * *

UNITED STATES PATENT AND TRADEMARK OFFICE
CERTIFICATE OF CORRECTION

PATENT NO. : 4,537,880
DATED : August 27, 1985
INVENTOR(S) : Hamao Umezawa et al.

It is certified that error appears in the above—identified patent and that said Letters Patent is hereby corrected as shown below:

In column 28, line 5, change "diphenylmethyl" to read --- diphenylethyl ---.

Signed and Sealed this

Thirty-first Day of December 1985

[SEAL]

Attest:

DONALD J. QUIGG

Attesting Officer  Commissioner of Patents and Trademarks